United States Patent [19]

Gauthier

[11] Patent Number: 5,295,964
[45] Date of Patent: Mar. 22, 1994

[54] HOLDER AND WARMER FOR IV SOLUTION CONTAINERS

[76] Inventor: Robert T. Gauthier, 136 NW. 79th St., Seattle, Wash. 98117

[21] Appl. No.: 770,501

[22] Filed: Oct. 2, 1991

[51] Int. Cl.$^5$ ............................................. A61F 7/12
[52] U.S. Cl. ..................................... 604/113; 604/408
[58] Field of Search ................. 606/27, 28; 604/113, 604/291, 93, 408, 404, 141, 174, 262; 128/204.17, 399, 400–403

[56] References Cited

U.S. PATENT DOCUMENTS

| | | | |
|---|---|---|---|
| 696,441 | 4/1902 | Holmes | 604/291 |
| 1,433,010 | 10/1922 | Hogan . | |
| 1,723,373 | 8/1929 | Roberts | 604/291 |
| 1,915,523 | 6/1933 | Ferguson . | |
| 1,975,329 | 10/1934 | MacSweeney | 128/399 |
| 2,220,777 | 11/1940 | Othmer . | |
| 2,289,425 | 7/1942 | Hogan . | |
| 2,339,409 | 1/1944 | Jay et al. | 604/291 |
| 2,590,212 | 3/1952 | Samuels | 604/291 |
| 3,093,308 | 6/1963 | Snelling . | |
| 4,077,390 | 3/1978 | Stanley et al. . | |
| 4,372,318 | 2/1983 | Viesturs et al. | 128/399 |
| 4,804,367 | 2/1989 | Smith et al. | 604/113 |
| 4,808,159 | 2/1989 | Wilson | 604/113 |
| 4,872,442 | 10/1989 | Manker . | |
| 4,934,336 | 6/1990 | White | 604/113 |

FOREIGN PATENT DOCUMENTS

| | | | |
|---|---|---|---|
| 8604810 | 8/1986 | World Int. Prop. O. | 604/291 |
| 9005508 | 5/1990 | World Int. Prop. O. | 604/291 |

Primary Examiner—John D. Yasko
Assistant Examiner—Manuel Mendez
Attorney, Agent, or Firm—Christensen, O'Connor, Johnson & Kindness

[57] ABSTRACT

An insulative cover is wrapped around a container of intravenous (IV) solution to assist in maintaining the solution at a desired temperature. The cover has an inside pocket for a heat pack that can be activated to warm the IV solution. A loop of hanging cord carried by the cover is insertable through a hole of the container for supporting the container from the cover.

2 Claims, 2 Drawing Sheets

HOLDER AND WARMER FOR IV SOLUTION CONTAINERS

BACKGROUND OF THE INVENTION

1. Field of the Invention

The present invention relates to a special holder for a standard container of intravenous (IV) solution for keeping the solution warm without inhibiting convenient dispensing of the solution from the container.

2. Prior Art

IV solutions usually are packaged in disposable bags of flexible clear plastic having holes at the top for hanging of the bags and couplings at the bottom for connection to standard IV tubes.

Sometimes it is desirable or necessary to administer an IV solution in a cold environment. The IV solution can cool quickly to the point where it is less than an ideal temperature for introduction into the body. In such a situation, the bag of IV solution may be stored in a warm location until immediately prior to use. Nevertheless, the solution may cool undesirably during the time that it is being administered. In emergency situations in cold climates, for example, it is difficult to maintain a desired temperature of the solution. Similarly, some surgical operations are conducted outdoors or in cool rooms, such as some veterinary operations, and maintaining IV solutions at desired temperatures can be difficult.

SUMMARY OF THE INVENTION

The present invention provides a special holder for a standard container of IV solution in the form of a folded insulative cover which may be wrapped around the container to assist in maintaining the container at a desired temperature. In the preferred embodiment, the cover has an inside pocket for receiving a heat pack that can be activated to warm the IV solution.

DETAILED DESCRIPTION

Figure 1:
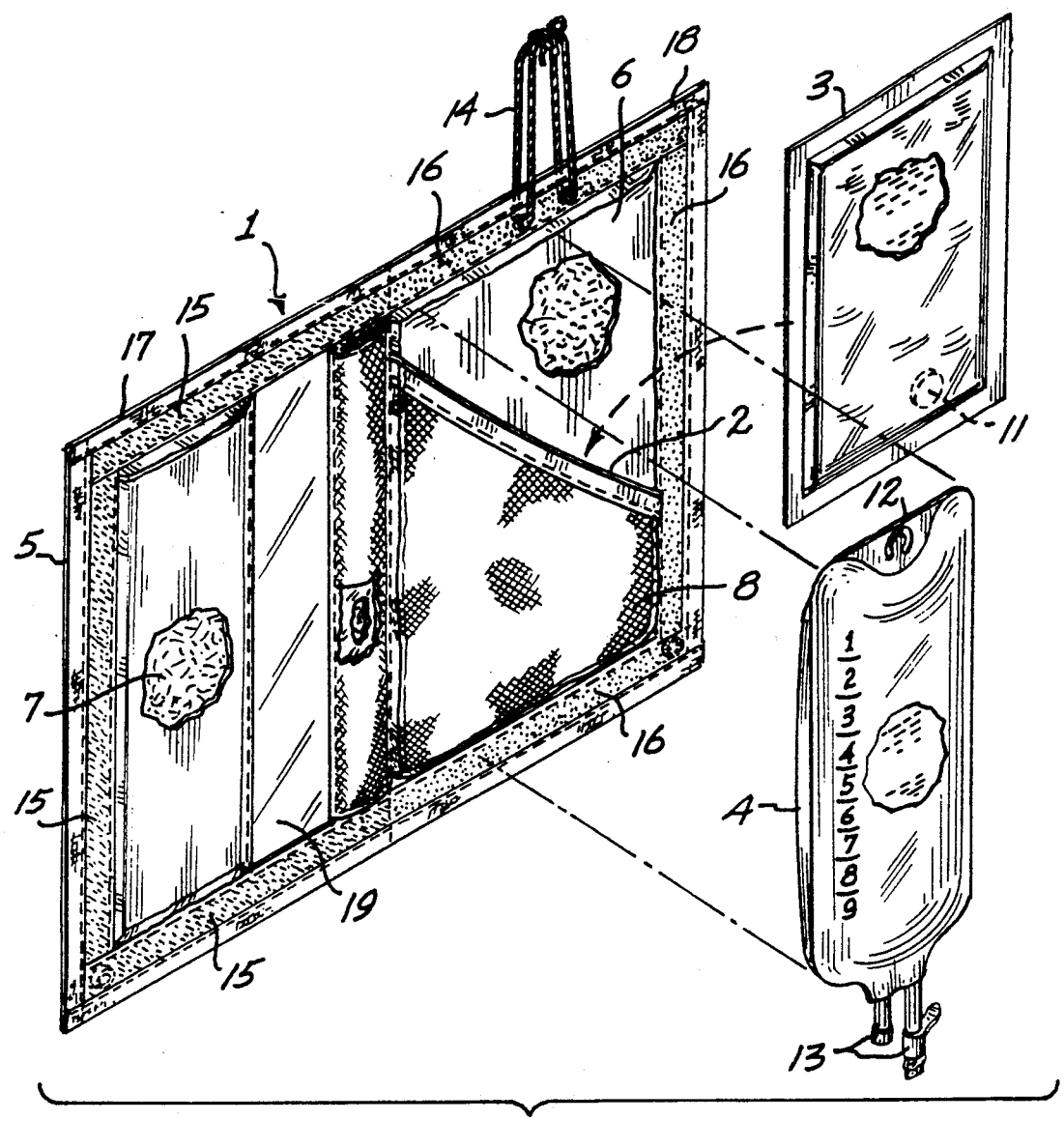
FIG. 1 is a top perspective of a standard container of IV solution and a holder-warmer in accordance with the present invention with parts shown in exploded relationship.

With reference to FIG. 1, the holder in accordance with the present invention consists of a special cover 1, preferably with an inside pocket 2 for a heat source in the form of a flat heat pack 3. In use, the cover is folded to the condition shown in FIG. 3 so as to be wrapped around a standard container 4 of IV solution. The cover substantially completely encloses the container 4 and deters heat loss. A positive warming action is achieved if the internal heat pack is activated.

The cover includes an outer sheet 5 of a flexible but tough weather and wear resistant fabric and an inner sheet 6 of a reflective flexible fabric or foil. One or more layers of insulative batting 7 are interposed between the two sheets 5 and 6. The sheets are sewn together along their margins and at spaced locations for retaining the batting and reinforcing the sheets without interfering with folding of the cover at its center to the condition shown in FIG. 3 in which the opposite end portions of the cover are disposed face-to-face.

Pocket 2 is formed by a smaller inside sheet 8 sewn along its sides and bottom to the remainder of the cover. Preferably, the pocket sheet 8 is a mesh material having openings for free conduction of heat from the heat pack through sheet 8 to the container 4 received in the holder. In the embodiment shown in FIGS. 1 through 4, the top edge of the pocket is inclined from about the vertical center of the holder to a location adjacent to the top of the holder such that the substantially flat rectangular heat pack 3 has the major portion of its volume received in the pocket. Nevertheless, an upper corner portion of the heat pack is exposed for easy removal from the pocket. The heat pack is snugly received in the pocket but is retained therein primarily by gravity.

Figure 5:
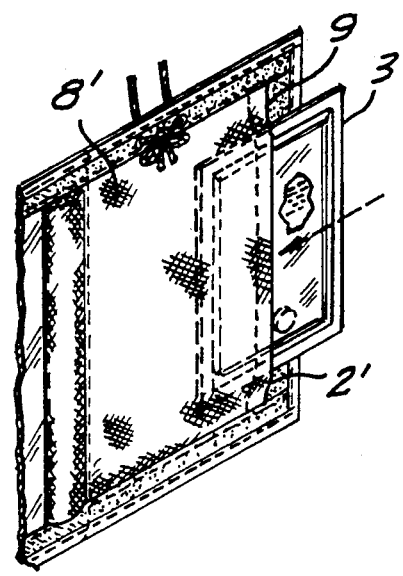
FIG. 5 is a fragmentary top perspective of a modified form of holder-warmer in accordance with the present invention.

In the modified form shown in FIG. 5, the inside pocket sheet 8' of mesh material is sewn along its top, bottom and inside vertical edges such that the entire outer side edge 9 of the pocket 2' can be opened for insertion of the heat pack 3. The heat pack can be inserted to a position in which its entire volume is received in the pocket. Preferably, suitable fasteners are provided along the outer pocket edge 9, such as continuous strips of hook-and-pile fasteners, for normally closing the pocket to secure the heat pack.

In other respects the embodiment of FIG. 5 is identical to the embodiment of FIGS. 1 through 4.

The heat pack preferably is of the general type described in U.S. Pat. No. 4,077,390. See also U.S. Pat. Nos. 1,433,010; 1,915,523; 2,289,425; 2,220,777; 3,093,308; and 4,872,442. In general, pack 3 includes inner and outer sheets of a clear plastic material having their margins secured together and containing a sodium acetate solution. Crystallization of such solution so as to generate heat can be activated by bending a metal button 11. Once activated the heat pack will continue to warm the IV solution for an extended period of at least several minutes. The actual warming period would depend on the amount of sodium acetate solution used, the starting temperature of the IV solution and its container and the ambient temperature. Preferably, the area of the side of the heat pack presented to the container is at least as great as the adjacent side of the container 4 so that heat is applied throughout substantially the entire adjacent side of the container.

In the embodiment illustrated in FIGS. 1 through 4, the cover in its flat condition is about 13-¼ inches high by about 18 inches long which is appropriate for enclosing a standard 1 liter container of IV solution. The illustrated container corresponds to the container sold under the trademark "Viaflex" by Baxter Health Care Corp. of Deerfield, Ill. Such container has an arcuate hole 12 at the top and couplings 13 at the bottom for connection of IV tubes.

Figure 2:
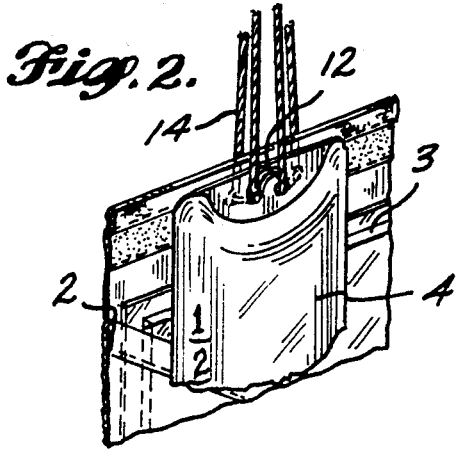
FIG. 2 is a fragmentary top perspective of the standard container and holder-warmer of FIG. 1 with the parts partially assembled.

Cover 1 is provided with a loop 14 of cord extending through holes in the top margin of the cover centered over the pocket 2. As illustrated in FIG. 2, the inside end portion of loop 14 can be inserted through the top hole 12 of container 4 for hanging the container centered over the heat pack 3 received in the pocket 2.

Figure 3:
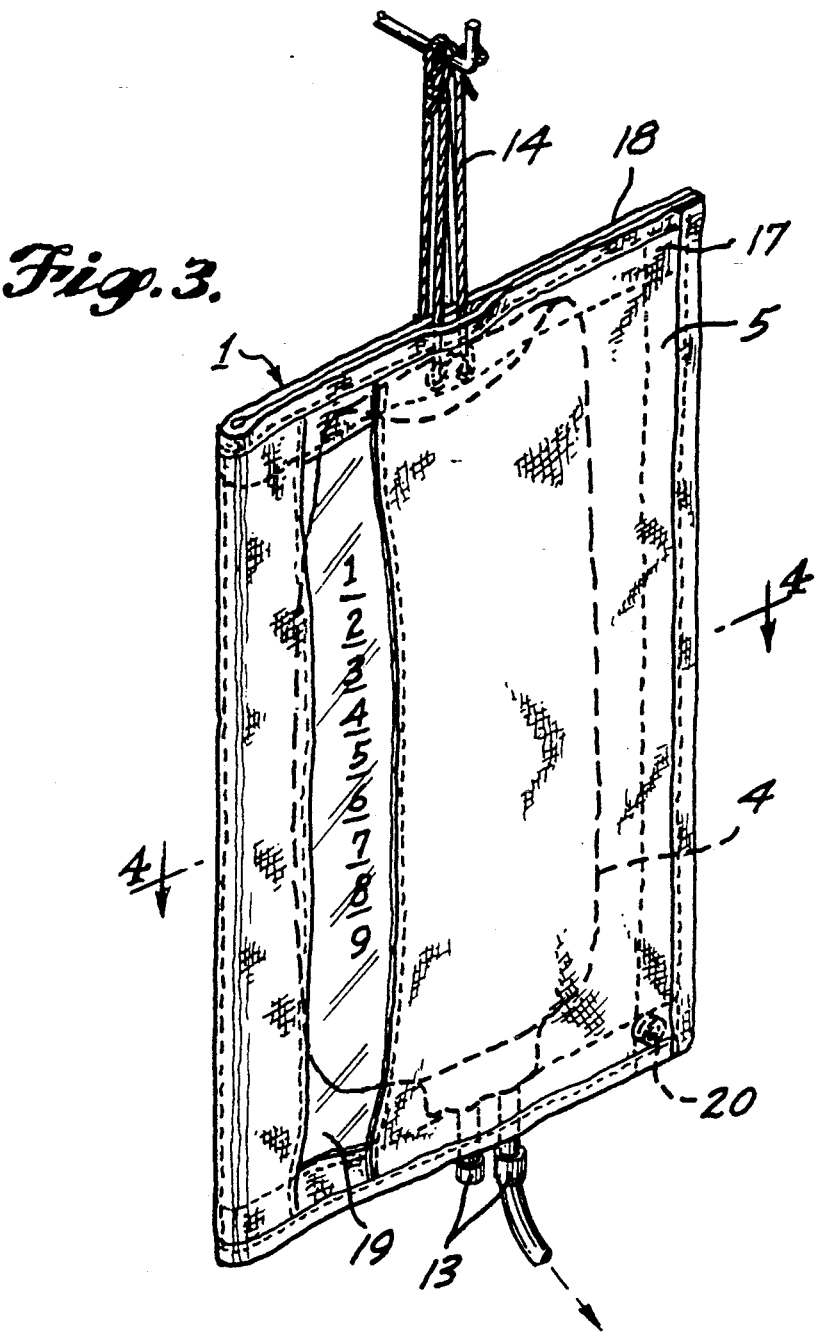
FIG. 3 is a top perspective of the standard container and holder-warmer in accordance with the present invention with the parts fully assembled.
Figure 4:
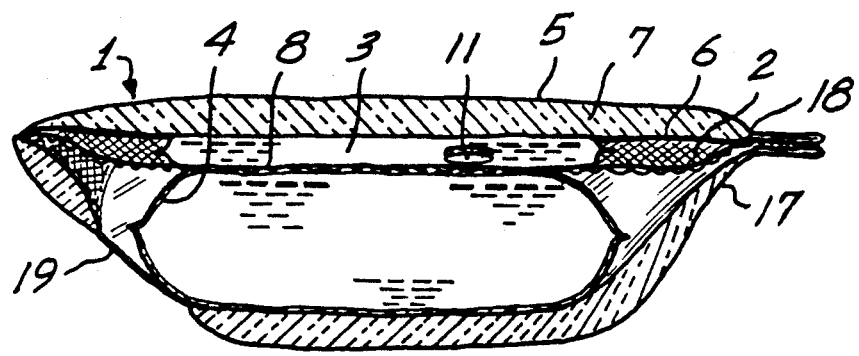
FIG. 4 is a section along line 4—4 of FIG. 3.

Next, the cover is folded about its center so as to enclose the container as illustrated in FIG. 3 except for the couplings 13 which project from the bottom.

Preferably, one end portion 17 of the cover has a continuous or substantially continuous strip 15 of hook-and-pile fastening material along its top, bottom and outside edges and the other end portion 18 has a continuous or substantially continuous complemental strip 16 along its top, bottom and outside edges so that the cover is fastened in its folded condition substantially completely enclosing the IV solution container. The interconnected cover and container can be hung by the cord loop 14 as illustrated in FIG. 3.

Preferably, the IV solution container is visible through the end portion 17 of the cover which is opposite the pocketed end portion 18 so that the quantity of solution remaining in the container can be monitored. For this purpose end portion 17 includes a long window 19 of heavy clear plastic material extending from closely adjacent to the bottom of the cover to closely adjacent to the top and positioned to be aligned with a vertical edge portion of the container 4. The window is sewn along all edges and preferably is several times narrower than the end portion 17 to deter heat loss through the window. In addition, as illustrated in broken lines in FIG. 4, end portion 17 can be provided with an insulated closure flap 17' joined to the front portion of the 17' is swingable over the window 19 to prevent heat loss. The flap can be held closed by long strips of complemental hook-and-edge pile fastening material extending along the free edge portion and top and bottom edges of the flap and along the top and bottom edges of the window and its longitudinal edge opposite the edge to which the flap 17' is sewn. Flap 17' can be opened for viewing the IV solution container through the window.

If desired, a more secure fastening of end portions 17 and 18 can be achieved by addition of snaps such as snap 20 shown in broken lines in FIG. 3 to assure that the cover remains closed. Nevertheless, the cover still can be opened manually for removal of an empty container or for insertion of a new heat pack, for example.

I claim:

1. A holder for a container of IV solution comprising a generally rectangular cover of flexible sheet material, said cover having inner and outer surfaces and opposite end portions, said cover being foldable intermediate said end portions to a closed condition with the inner surfaces of said end portions disposed face-to-face and with the container therebetween for deterring heat loss from the container, a generally rectangular inner sheet having top, bottom and opposite upright side edges, said inner sheet being fastened along three of said top, bottom and opposite upright side edges to said inner surface of one of said end portions of said cover so as to form an inside pocket openable along the fourth of said edges, a heat source received in said pocket for warming the container, fastening means for normally maintaining the cover in its closed condition, the end portion of the cover opposite the end portion having the inside pocket having a window for viewing the container therethrough, and a flap movable to a position covering the window for deterring heat loss therethrough.

2. The holder defined in claim 1, including manually releasable fastening means for normally holding the flap in position covering the window.

* * * * *

UNITED STATES PATENT AND TRADEMARK OFFICE
CERTIFICATE OF CORRECTION

PATENT NO. : 5,295,964
DATED : March 22, 1994
INVENTOR(S) : R. T. Gauthier

It is certified that error appears in the above-indentified patent and that said Letters Patent is hereby corrected as shown below:

| COLUMN | LINE | |
|---|---|---|
| 3 | 28 | after "the" (first occurrence) insert --cover along one longitudinal edge of the window. Flap-- |

Signed and Sealed this

Nineteenth Day of July, 1994

Attest:

BRUCE LEHMAN

Attesting Officer   Commissioner of Patents and Trademarks